United States Patent [19]
Mannschedel

[11] Patent Number: 6,126,446
[45] Date of Patent: *Oct. 3, 2000

[54] COMPOSITION FOR FILLING TOOTH ROOT CANALS

[75] Inventor: Werner Mannschedel, Langenau, Germany

[73] Assignee: Roeko GmbH & Co., Dentalerzeugnisse, Germany

[*] Notice: This patent is subject to a terminal disclaimer.

[21] Appl. No.: 09/296,016

[22] Filed: Apr. 21, 1999

[30] Foreign Application Priority Data

Apr. 22, 1998 [DE] Germany .................. 198 17 844

[51] Int. Cl.[7] .................. A61C 5/00; C08G 63/02
[52] U.S. Cl. .................. 433/228.1; 433/226; 528/272
[58] Field of Search .................. 433/226, 228.1; 528/272

[56] References Cited

U.S. PATENT DOCUMENTS 4,632,977  12/1986  Riazi .................. 528/502

OTHER PUBLICATIONS

Friedman et al. In 5. Dent. Res., 54 (1975) pp. 921–925.

*Primary Examiner*—Terressa M. Boykin
*Attorney, Agent, or Firm*—Brian J. Laurenzo; Michael C. Gilchrist

[57] ABSTRACT

The present invention relates to a composition for filling tooth root canals comprising an isoprene-based powder and at least one sealer. The composition can be prepared by cooling an isoprene-based material, adding any additives that may be present before, during or after comminution, comminuting and then adding a sealer.

21 Claims, No Drawings

COMPOSITION FOR FILLING TOOTH ROOT CANALS

FIELD OF THE INVENTION

The present invention relates to a composition for filling tooth root canals comprising an isoprene-based powder and at least one sealer.

BACKGROUND ART

For the treatment of a disorder known as pulpitis, the diseased pulpa is removed mechanically from the root canal and the root canal is cleaned and drilled out, filled with an elastic-plastic element or with a different filling material and then sealed. An ideal root canal filling material should not irritate the periapical tissue, should close the root canals sealingly laterally and vertically, its volume should remain stable and it should not shrink in the root canal. For the prior art, see, for example, Friedman et al. In J. Dent. Res., 54 (1975) 921–925, Briseno in Philipp J., 2, 90, 65–73 and U.S. Pat. No. 4,632,977. As root canal filling materials, Briseno describes inter alia semi-rigid cements based on synthetic resin, zinc oxide eugenol, calcium hydroxide or glass ionomer. U.S. Pat. No. 4,632,977 proposes filling materials based on tans-polyisoprene, for example based on gutta-percha or balata. Gutta-percha points are commercially available, the standard composition thereof being 20% by weight of gutta-percha as matrix, from 60 to 75% by weight of zinc oxide as filler, from 1 to 17% by weight of heavy metal sulphates as X-ray contrast agent and from 3 to 4% by weight of waxes and resins as softener. That known filling material is inert in the root canal and accordingly does not react with body tissue.

Such gutta-percha points are usually introduced into the root canal by so-called vertical or lateral condensation.

In vertical condensation, a gutta-percha point is inserted into the root canal and its position in the canal is monitored by means of X-ray imaging. A sealer is then introduced into the canal, together with the gutta-percha, and the root canal is completely filled by alternate insertion and condensation of the thermoplastic gutta-percha in a number of working operations. Heated and softened gutta-percha can also be inserted into the root canal on a carrier point. Finally, molten gutta-percha can be inserted using a gutta-percha gun.

That method has the disadvantage, however, that the heat may denature the tissue surrounding the tooth and thus damage it. Moreover, the gutta-percha may be oxidized and/or degraded or cracked during heating. In particular, repeated hating of gutta-percha may result in degrading and thus ageing of the material.

In lateral condensation, gutta-percha points are introduced in succession into a root canal and are pressed against the sides of the root canal until the root canal is completely full. A disadvantage of that method is that the gutta-percha points must be pressed into the root canal with a certain application of force, which may result in fracture of the teeth. In addition, in vertical condensation, there is the risk of pressing too hard, as a result of which gutta-percha points may be pushed into the periapical tissue, which may lead to irritation or even to inflammation there.

The film thickness of the sealer is also important. In lateral condensation it is not, however, possible to set this precisely.

SUMMARY OF THE INVENTION

According to the invention, a composition for filling tooth root canals will therefore be provided comprising an isoprene-based powder and at least one sealer.

DISCLOSURE OF THE INVENTION

Preferably the isoprene-based powder is trans-polyisoprene, gutta-percha, balata or a mixture thereof, with gutta-percha powder being preferred. In the description of the present invention, the term "gutta-percha" is to include also isoprene, trans-polyisoprene or balata. Preferably, however, it denotes only gutta-percha itself. Gutta-percha is preferably trans-polyisoprene.

According to the invention, it is also possible to use compositions having different gutta-percha: sealer weight ratios of from 50:50 to 10:90: for example, a composition having a gutta-percha:sealer ratio of 50:50 may be used as the lowest layer and on top of that there may be used a composition that has a different gutta-percha:sealer ratio of, for example 30:70.

Such a layered structure combines optimum biocompatibility with a gutta-percha:sealer ratio that is ideal for adhesion to the tooth and for the cohesion of the mass. Uniform coverage of the root canal with sealer is also possible, with the result that good adhesion of the filing material to the tooth is provided, especially since a more homogeneous filling is possible with the composition according to the invention than with gutta-percha points, since the spaces between the powder particles are smaller.

According to a preferred embodiment, the isoprene-based powder according to the invention comprises at least 80% by weight of trans-polyisoprene.

According to the invention, a root canal can also be filled with the composition according to the invention and with one or more gutta-percha points that are customary per se.

According to the invention, the isoprene-based powder preferably has a particle size of up to 100 um, especially up to 50 um, more especially from 5 to 30 um and very especially from 10 to 20 um. According to the invention, the gutta-percha powder may have a particle size of, for example, from 15 to 20 um. According to the invention smaller particle sizes may be used however. Depending on the particle size, the isoprene-based material may be in the form of granules or coarse particles.

If the powder has a particle size of more than 100 um, it will no longer fit into fine lateral canals of the root canals; it is, however, currently, technically possible only with difficulty to obtain a particle size of less than 5 um.

Preferably the sealers used in combination with the gutta-percha powder are so selected that they are insoluble in water since otherwise resorption of the sealer can occur, which is undesirable from a physiological point of view. Moreover, erosion of the sealer causes lesions in the filling material, which may result in renewed bacterial attack on the root canal. To ensure that the gutta-percha powder remains firmly in the filling material, it is preferable for it to be insoluble in the sealer(s) used.

As sealers there may be used customary sealers comprising synthetic resins, such as epoxy bisphenols, eugenol, silicones, etc. Such sealers comprise, for example, commercially available silicone sealers of the single- or two-component type, wherein one of the two components may comprise a catalyst, such as a platinum compound. The sealers disclosed in DE 197 09 531.3 are especially preferred.

The composition according to the invention also has the advantage that the biologically acceptable gutta-percha, which was hitherto used only with difficulty and involving a large number of working steps, is provided in a form that considerably simplifies its introduction into the root canals.

According to the invention, the total composition preferably comprises at least 1% by weight of trans-polyisoprene and up te 99% by weight of sealer. Preferably there are used at least 20% by weight, specially at least 30% by weight, more especially at least 40% by weight, very especially at least 50% by weight, of sealer and most especially enough sealer for the selected gutta-percha powder in the desired particle size to have optimum physiological and adhesive properties in any selected layer in the root canal. The appropriate ratios can be determined by persons skilled in the art by means of a few experiments.

The composition according to the invention may additionally comprise customary additives, such as fillers, pharmaceutical active ingredients, X-ray contrast agents, dyes, such as iron oxides, waxes, surfactants, fatty acids, such as stearic acid, anti-oxidants, titanium dioxide and magnesium oxide, or mixtures thereof.

As fillers there may be used substances that are customary per se, such as zinc oxide and/or calcium hydroxide, in amounts that are customary per se.

There come into consideration as pharmaceutical active ingredients especially active ingredients that are soluble or dispersible in an aqueous medium, for example an antibiotic and/or glucocorticoid. A composition according to the invention may be characterized preferably by:

(a) up to 50% by weight of gutta-percha powder,
(b) up to 99% by weight of sealer,
(c) up to 70% by weight of filler,
(d) up to 70% by weight of X-ray contrast agent, based on (a) and (b), and
(e) optionally additional customary components.

Thus, the composition according to the invention may be characterized, for example, by (a) up to 50% by weight of gutta-percha powder,
(b) up to 50% by weight of sealer,
(c) up to 50% by weight of zinc oxide,
(d) up to 50% by weight of X-ray contrast agent, based on (a) and (b), and
(e) optionally additional customary components.

Finally, according to a further embodiment of the invention, a method is provided for preparing the composition according to the invention, which method is characterized in that an isoprene-based material is comminuted and optionally additives are added thereto before, during or after comminution. The powder can then be mixed with one or more sealers or components thereof.

Various methods may be used to comminute gutta-percha, for example spraying of molten or dissolved gutta-percha in a spray tower, polymerization in a non-solvent, customary precipitation methods or preferably grinding at low temperatures. For that purpose, gutta-percha is cooled, for example with liquid nitrogen, to low temperatures of down to −270° C. and is then ground until the desired particle diameter, for example from 15 to 20 um, has been reached.

Such a gutta-percha powder can be readily applied, in combination with a viscous sealer, with a syringe, penetrates well into fine lateral canals and provides good contact against the tooth walls. Heating or vigorous repacking with a plugger can be omitted.

The compositions according to the invention may comprise, in addition to the isoprene-based powder and the sealer, further organic and inorganic substances which are added—all at once or in several portions—before, during or after granulation or grinding.

The composition according to the invention has, however, basically three components, which will be explained hereinafter in greater detail.

Component 1

The mechanical properties of the powder that can be prepared according to the invention are determined primarily by the properties of the isoprene-based material. The powder should be able to take up other components readily, especially a filler and optionally and X-ray contrast agent. For those purposes, a matrix comprising at least 80% by weight of trans-polyisoprene has proved advantageous. Gutta-percha may be mentioned by way of example, which is a naturally based matrix, the main component of which is trans-polyisoprene. Other trans-polyisoprenes may of course also be used, such as balata, synthetic isoprene-based matrices or derivatives of the mentioned materials.

Component 2

The composition according to the invention may also comprise fillers, such as zinc oxide and/or calcium hydroxide. Those fillers are present in an amount, based on the total composition, of, for example, up to 80% by weight together with up to 50% by weight of isoprene based material. Calcium hydroxide is a substance that is tolerated by tissue and the body and which can be mixed with the matrix and compounded additionally with pharmaceutical active ingredients and customary auxiliaries. Zinc oxide can be rolled in powder form into gutta-percha, which greatly simplifies the preparation process. The proportion of zinc oxide is then based upon the amount of gutta-percha powder and its capacity to take up a filler. An example of a composition having a very high proportion of filler is a gutta-percha powder comprising about 70% by weight of zinc oxide together with about 30% by weight of gutta-percha.

Component 3

As a further optional (although customary) component, an X-ray contrast agent may be selected from the group consisting of zinc, ytterbium, yttrium, gadolinium, zirconium, strontium, tungsten, tantalum, niobium, barium, bismuth, molybdenum and lanthanum powders, powdered alloys thereof, oxides, fluorides, sulphates, carbonates, tungstates and carbides thereof, and mixtures thereof. That component may be provided in an amount of up to 70% be weight, preferably up to 50% by weight, more especially up to 30% by weight, based on the composition.

The following example is intended to illustrate, but not limit, the invention:

EXAMPLE

To prepare gutta-percha powder, gutta-percha as matrix was first rolled between a carrier roller and a pressure roller, so that the gutta-percha lay around the carrier roller in the form of a thin film or like a skin. Powdered zinc oxide and powdered zirconium oxide in a weight ratio of 30% gutta-percha:55% zinc oxide:15% zirconium oxide were then rolled into the film that had been produced, the film was peeled away from the carrier roller and the peeled-away film was comminuted and extruded to a strand. The strand was then cut up and comminuted, cooled with liquid nitrogen to a temperature of −270° C. and then ground to a particle diameter of about 20 um. 2 g of the resulting powder were then added to each component of a two-component sealer. In each component, powder:sealer were present in a ratio of 40:60. The two components are combined and mixed directly before use.

The product can be easily introduced into a canal, and also enables insertion of a gutta-percha point and seals off the canal well.

What is claimed is:

1. A composition for filling tooth root canals comprising an isoprene powder and at least one sealer.

2. The composition according to claim 1, characterized in that the isoprene powder is selected from the group consisting of trans-polyisoprene, gutta-percha, balata powder, and any mixture thereof.

3. The composition according to claim 1, characterized in that the isoprene containing powder comprises at least 80% by weight of trans-polyisoprene.

4. The composition according to claim 1, characterized in that the powder has a particle size of up to 100 um.

5. The composition according to claim 1, characterized in that the powder has a particle size ranging from 10 to 30 um.

6. The composition according to claim 1, characterized in that the sealer is insoluble in water.

7. The composition according to claim 1, characterized in that it the composition comprises up to 50% by weight of trans-polyisoprene powder and up to 99% by weight of sealer.

8. The composition according to claim 1, characterized in that the isoprene powder comprises one or more customary additives selected from the group consisting of fillers, pharmaceutical active ingredients, X-ray contrast agents, waxes, resins, surfactants and any mixture thereof.

9. The composition according to claim 8, characterized in that the isoprene powder comprises a filler that comprises calcium hydroxide, zinc oxide, aluminum oxide, silicon dioxide or mixtures thereof.

10. The composition according to claim 8, characterized in that the isoprene powder comprises a pharmaceutically active ingredient that is soluble or dispersible in aqueous media.

11. The composition according to claim 10, characterized in that the pharmaceutically active ingredient is an anti-bacterially active composition.

12. The composition according to claim 11, characterized in that the anti-bacterially active composition is selected from the group consisting of antibiotics, glucocorticoid, and mixtures thereof.

13. The composition according to claim 8, characterized in that the isoprene powder comprises an X-ray contrast agent selected from the group consisting of zinc, ytterbium, yttrium, gadolinium, zirconium, strontium, tungsten, tantalum, niobium, barium, bismuth, molybdenum and lanthanum powders, powdered alloys thereof, oxides, fluorides, sulphates, carbonates, tungstates and carbides thereof, and mixtures thereof.

14. The composition according to claim 1, characterized in that all the components except the sealer are present in the form of a powder or a viscous mass.

15. The composition according to claim 1 comprising:
    (a) between 0 and 50% by weight of gutta-percha powder,
    (b) between 0 and 99% by weight of sealer,
    (c) up to 70% by weight of filler,
    (d) up to 70% by weight of X-ray contrast agent, based on (a) and (b), and
    (e) optionally additional customary components.

16. The composition according to claim 15, comprising:
    (a) between 0 and 50% by weight of gutta-percha powder,
    (b) between 0 and 50% by weight of sealer,
    (c) up to 50% by weight of zinc oxide,
    (d) up to 50% by weight of X-ray contrast agent, based on (a) and (b), and
    (e) optionally additional customary components.

17. A method for the preparation of a composition for filling tooth root canals comprising an isoprene powder, at least one sealer, and one or more additives comprising the following steps:
    (a) comminuting the isoprene material;
    (b) adding the additives which may be present before, during or after comminution to form a mixture; and
    (c) mixing the mixture with at least one sealer.

18. The method according to claim 17, wherein, prior to comminuting the isoprene material, the isoprene material is cooled to at least −40° C.

19. The method according to claim 18, wherein, prior to comminuting the isoprene material, the isoprene material is cooled to at least −200° C.

20. The method according to claim 19, wherein, prior to comminuting the isoprene material, the isoprene material is cooled to at least −270° C.

21. The method according to any one of claims 18, 19 and 20, wherein the isoprene-based material is ground to a particle size of less than or equal to 100 μm after cooling.

* * * * *